United States Patent
Sonnleitner

(10) Patent No.: US 8,580,194 B2
(45) Date of Patent: Nov. 12, 2013

(54) DEVICE FOR OPTOELECTRONICALLY CHARACTERIZING SAMPLES

(75) Inventor: Max Sonnleitner, Linz (AT)

(73) Assignee: ASMAG-Holding GmbH (AT)

( * ) Notice: Subject to any disclaimer, the term of this patent is extended or adjusted under 35 U.S.C. 154(b) by 281 days.

(21) Appl. No.: 12/312,767

(22) PCT Filed: Nov. 23, 2007

(86) PCT No.: PCT/EP2007/010158
§ 371 (c)(1),
(2), (4) Date: Apr. 26, 2010

(87) PCT Pub. No.: WO2008/061771
PCT Pub. Date: May 29, 2008

(65) Prior Publication Data
US 2010/0202922 A1   Aug. 12, 2010

(30) Foreign Application Priority Data
Nov. 23, 2006   (DE) .......................... 10 2006 055 877

(51) Int. Cl.
*G01N 33/00* (2006.01)
(52) U.S. Cl.
USPC ..................... 422/52; 422/82.06; 422/68.1
(58) Field of Classification Search
USPC ...................... 422/52, 68.1, 82.06
See application file for complete search history.

(56) References Cited

U.S. PATENT DOCUMENTS

| | | |
|---|---|---|
| 5,589,136 A | 12/1996 | Northrup et al. |
| 6,136,268 A | 10/2000 | Ala-Kleme et al. |
| 6,207,369 B1 | 3/2001 | Wohlstadter et al. |

FOREIGN PATENT DOCUMENTS

| | | |
|---|---|---|
| DE | 69634175 T2 | 1/2006 |
| EP | 1249705 A2 | 10/2002 |
| GB | 2369428 | 5/2002 |
| WO | 2006026796 A1 | 3/2006 |

OTHER PUBLICATIONS

International Search Report, PCT/EP2007/010158, dated Mar. 20, 2008.
Knight A W: "A review of recent trends in analytical applications of electrogenerated chemiluminescence" TRAC, Trends in Analytical Chemistry, Elsevier, Amsterdam, NL, vol. 18, No. 1, (Jan. 1999), pp. 47-62.
Hsueh Y-T et al: "DNA quantification with an electrochemiluminescence microcell" Sensors and Actuators B, Elsevier Sequoia S.A., Lausanne, OH, vol. 49, No. 1-2, (Jun. 25, 1998), pp. 1-4.
Cheng et al: "Microchip-based devices for molecular diagnosis of genetic diseases" Molecular Diagnosis, Naperville, IL, US, vol. 1, No. 3, (Sep. 1996), pp. 183-200.
Hsueh: "Microfabricated, electrochemiluminescence cell for the detection of amplified DNA" International Conference on Solid-State Sensors, vol. 1, (Jun. 25, 1995), pp. 768-769.

*Primary Examiner* — Sam P Siefke
(74) *Attorney, Agent, or Firm* — Lerner, David, Littenberg, Krumholz & Mentlik, LLP

(57) ABSTRACT

Device (1) for optoelectronically characterizing samples by means of electrochemiluminescence (ECL), in which an electric voltage applied across a counter electrode (6) and a working electrode (2) on which the sample spots are disposed excites the sample to luminescence and a reading of the luminescence is taken using an optoelectronic component, characterized in that the optoelectronic component comprises an image detection component (4) with a photoactive layer (10) made from organic semiconductors between two electrode layers (11,14).

11 Claims, 2 Drawing Sheets

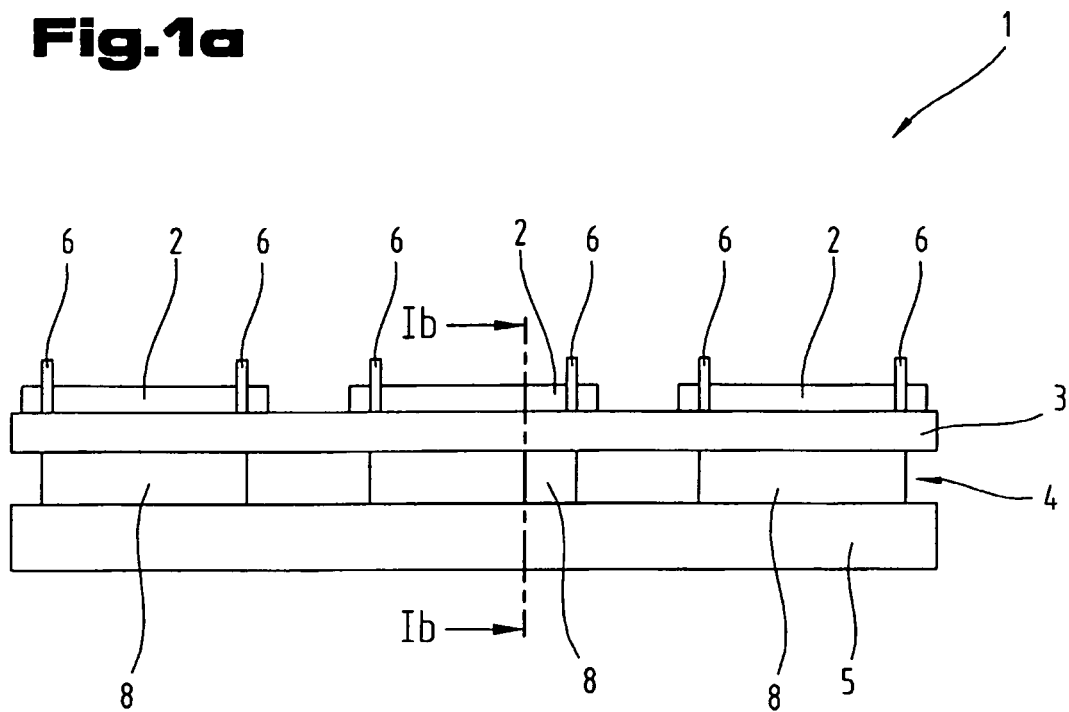
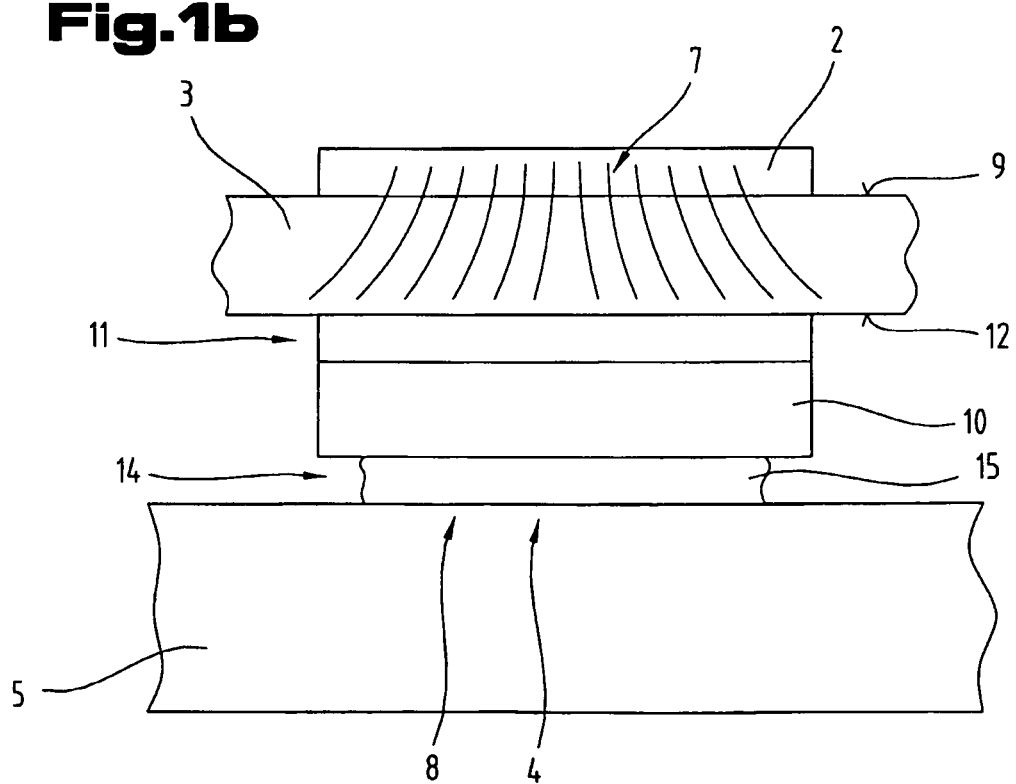

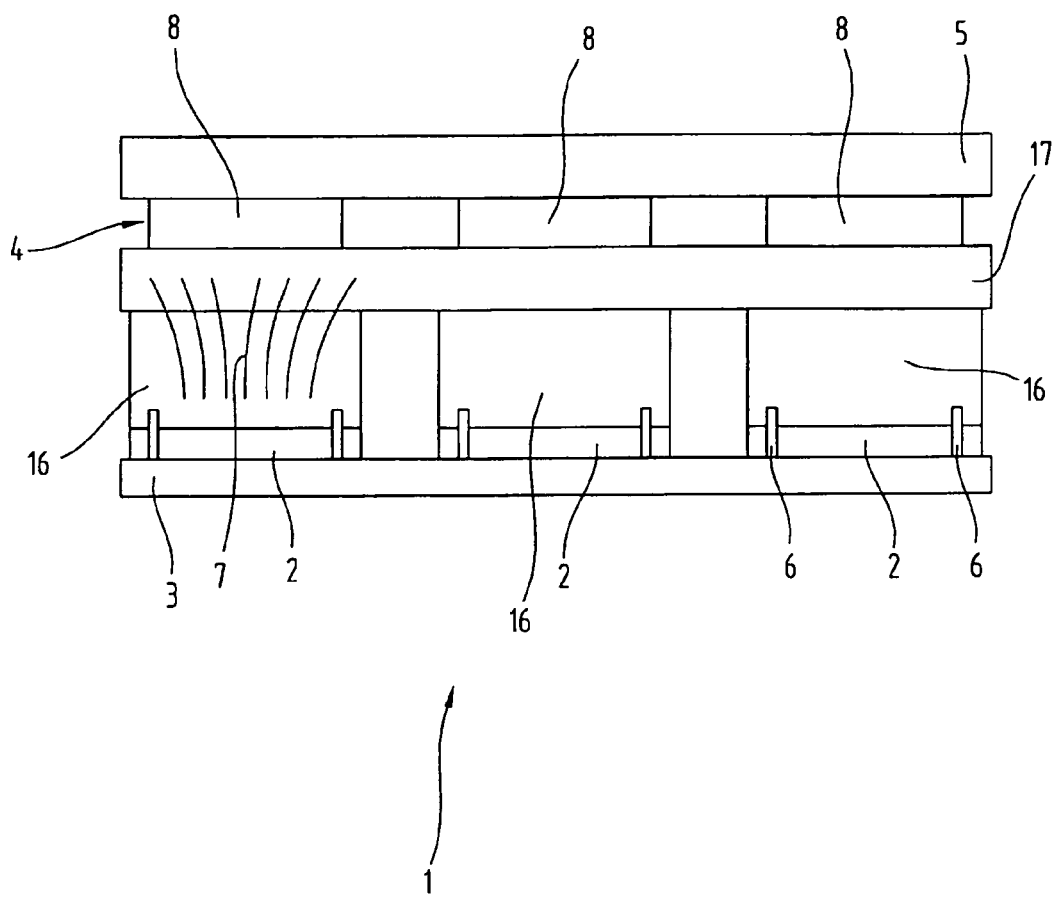

DEVICE FOR OPTOELECTRONICALLY CHARACTERIZING SAMPLES

The present application is a national phase entry under 35 U.S.C. §371 of International Application No. PCT/EP2007/010158, filed Nov. 23, 2007, published in English, which claims the benefit of German Patent Application No. 10 2006 055 877.4, filed Nov. 23, 2006. The disclosures of the above applications are incorporated by reference herein.

The invention relates to a device for optoelectronically characterizing samples by means of electrochemiluminescence (ECL), in which an electric voltage applied across a counter electrode and a working electrode on which the sample spots are disposed excites the sample to luminescence and a reading of the luminescence is taken using an optoelectronic component.

The concept of luminescence as used here includes the optical radiation of a physical system which is generated during the transition from an excited state to the basic state.

A distinction is made between different types of luminescence according to the type of excitation, for instance photoluminescence, where excitation is caused by photons, or thermoluminescence where excitation is caused by heat. Chemiluminescence is also known and commonly used as a means of testing blood samples, for instance when testing samples for HIV.

If excitation is induced by applying voltage, it is known as electrochemiluminescence, or ECL for short.

With ECL stable precursors are placed onto the surface of an electrode, which react with each other and thus emit light.

The advantage of electrochemiluminescence over processes which use light excitation is that no light scattering occurs. Light scattering is a disadvantage in that it makes it more difficult to take an actual reading of the luminescence because the scattered light leads to measurement errors in the absence of appropriate filtering.

Another disadvantage of electrochemiluminescence is that the intensity of the emitted electromagnetic radiation is directly proportional to the intensity of the reaction and to the quantity of the sample material to be identified. Other known processes for identifying samples based on the effects of luminescence require at least one source of electromagnetic radiation in order to excite the sample to be tested, and if necessary to detect weakening reactions. With such processes, the reaction intensity is always determined by measuring a secondary para-meter that is also affected. Due to the imprecise amount of electromagnetic radiation emitted from the source and also due to scattering effects, even small discrepancies could lead to considerable distortion of the measurement results. Especially with very weak reactions, there is the risk that negative effects such as undesired scattering might mask the very weak reaction and thus prevent it from being detected. Since no additional light sources are provided or needed with electrochemiluminescence, it enables even very weak reactions to be detected accurately and reliably.

Other advantages are the fact that only those labels of molecules that are bound to the electrodes emit light and these labels exist for very many biomolecules.

For example, the labels may include biomolecules from the group including ruthenium (II) chelate Ru (bpy) 32+Tb (III) chelate, 9-fluorenylmethyl chloroformate, fluorescine derivatives and similar materials, aromatic lanthanide (III) chelate, various coumarines and porphyrins.

Furthermore, multiple excitation cycles could result in an amplification of the signal, ultimately achieving emissions of 620 nm, in other words at a wavelength that is very transparent for biological media.

However, these advantages are also offset by significant disadvantages.

To date, samples have been excited using a carbon electrode as the working electrode, which on the one hand has the advantage that the molecules bind themselves non-specifically thereon and do not deteriorate, in other words they remain functional.

On the other hand, since the carbon electrode is not transparent, a readout can only be obtained by sensor systems positioned above the sample. This requires relatively large readout units.

Since it is standard practice to use CCD cameras for the readout, another disadvantage is the fact that these systems become very complex and expensive, the bigger they are.

This applies not only to the cameras themselves, but also to their movement system.

Then again, there are also problems when a very compact solution is required, particularly with the imaging optics, movement system and finally the microtiter plates.

Devices are known from the prior art in which the optical analysis component is provided in the form of an image detection unit with upstream optics, and the image detection unit can be specifically and controllably positioned with a positioning mechanism to enable the numerous reaction areas to be imaged. In order to obtain reproducible results, it is absolutely vital to be able to control the imaging area repeatedly and unambiguously, which results in considerable construction complexity. One thing which many of the known devices have in common is that the device used to take electrochemiluminescence measurements is not an integrated component of the analysis device and instead has to be inserted or placed in it, for example. This requires additional work steps and presents the risk of distorted results and damage to the sample. In particular during the required insertion of the measurement device in the analysis device, the analysis device could become contaminated by the sample material and thus require a complex cleaning process.

Another disadvantage of the known devices is that they are typically rather large due to their complex construction and thus not well suited to mobile applications.

From WO 2006/026796 a device is known, by means of which bio-chemical samples such as microarrays can be analyzed.

This device comprises a sample holder along with an image detection unit. This image detection unit has a photoactive layer made from an organic semiconductor between two electrode layers, of which the electrode layer between the photoactive layer and samples is at least partially translucent. This image detection unit may be applied directly onto the surface of the biochip opposite the microarray, thereby obviating the need for precise process mechanisms and complex imaging optics such as used in conventional readout systems.

The underlying objective of the invention is to propose a device for optoelectronically characterizing samples, by means of which the disadvantages of readout systems used for ECL to date can be avoided.

This objective is achieved by the invention with a device as defined in claim 1.

Preferred embodiments are defined in the dependent claims.

A core concept of the invention is the use of an optoelectronic image detection component based on an organic semiconductor to take a reading of the luminescence.

Such an image detection device has a number of important advantages.

For instance, the advantage of organic semiconductors is that they can be manufactured without energy intensive processes such as high vacuum processes or high temperature vacuum deposition processes. Another advantage of organic semiconductors is that their disposal does not have any detrimental impact on the environment to speak of. Furthermore, the spectral efficiency of organic semiconductors can be targeted to the specific electromagnetic radiation of electrochemiluminescence to be detected, for instance through so-called bandgap engineering. From an economic standpoint, it is particularly important that organic semiconductors are especially cost-effective and efficient to manufacture.

Also of advantage is the very compact construction which, depending on the working electrode, permits positioning either above or below the working electrode.

In one advantageous embodiment, the biocompatible material is made from TCOs (transparent conductive oxides), thin metal layers, or very good conductors such as polyaniline (PANI) and poly-3,4-ethylene dioxythiophene (PEDOT). TCOs such as indium tin oxide (ITO), for example, have the advantage that they combine well with organic semiconductor materials, provide good electrical conductivity with sufficient transparency and enable electrodes to be manufactured inexpensively.

If a transparent but nevertheless biocompatible working electrode is used, the optoelectronic image detection component can be placed underneath the working electrode.

A significant advantage of the image detection component based on an organic semiconductor is that there are no constraints as to surface dimensions. There are no problems in manufacturing these semiconductor arrangements in any desired size and then installing them.

Carbon nanotubes are particularly well suited as transparent, biocompatible electrodes.

By carbon nanotubes is meant tube-like carbon structures, comprising closed, cylindrically shaped graphite planes with a diameter of 1-10 nm. They can be activated by applying electric voltage.

A transparent electrode must be transparent or semitransparent at least in the spectral range corresponding to the wavelength of the electromagnetic radiation of the electrochemiluminescence to be detected. Also particularly well suited as transparent or semitransparent electrodes are thin metal layers, in which case a gold layer up to 30 nm thick is semitransparent and a very good electrical conductor, for example.

The optoelectronic image detection component can be placed directly underneath the working electrode, and a substrate in the form of a glass carrier is placed between the working electrode and the image detection component. This enables an extremely compact construction to be obtained.

The substrate may also be made from plastic such as PET, COC, PS, PC, PP or PMMA, for example. In particular, the substrate or at least its surface is electrically non-conductive and if necessary, an electrical isolating layer may be applied to the substrate. With such a substrate, the image detection component can be placed directly on a flat face of the substrate without the risk of electrical interaction between the image detection component and the substrate.

This is also possible with the second variant, namely if a non-transparent working electrode is used.

In this case, a readout of the luminescence is taken from above, i.e. the optoelectronic image detection component based on an organic semiconductor is positioned above the working electrode.

In this case, however, the term above means a position directly above the working electrode, so that this variant also offers an extremely compact construction.

The essential aspect is that this system also places no limitations on the spatial dimensions of the system's construction.

An especially advantageous embodiment can be obtained if the image detection component is printed onto a substrate, because organic semiconductors can be manufactured in an advantageous manner with printing processes. Printing processes include inkjet, screen printing or stamp printing, for example, and all of these processes are additive structuring processes. This is in contrast with the manufacture of inorganic semiconductors based on subtractive structuring processes, which are more complex and more expensive to use and by means of which very complicated structures are difficult or impossible to manufacture. Printing processes have the further advantage of requiring no complex and energy intensive work environments or work processes. In terms of manufacturing costs, printed organic semiconductors have the further advantage that material is placed in a very targeted manner and much less material is therefore required than is the case with inorganic semiconductors.

Another, very important advantage resides in the fact that organic semiconductors can also be printed retroactively onto a prefabricated sample device, the sample spots. This is of particular advantage if the sample device is produced by a first manufacturer and the image detection component is then applied using a printing process in a second step. The printing processes used can be flexibly configured so that the imaging device can be printed onto almost all known sample devices.

The advantage of a transparent or semitransparent substrate is that it allows the electromagnetic radiation emitted by electrochemiluminescence to act on the imaging component unhindered. Another advantage is that the substrate can serve as a mechanical support for the electrochemiluminescence device, for example.

In one advantageous embodiment, the substrate is electrically non-conductive and has an electrically non-conductive surface so that the electrode layer can be applied directly onto the substrate.

An image detection component comprising a plurality of quantum detectors, for instance phototransistors, photodiodes or photoresistors, has the advantage that the spectral efficiency of the quantum detectors can be readily adapted to the electromagnetic radiation to be detected.

Electrode layers formed by finger electrodes, arranged so that their lengths are oriented in different directions from each other, have the particular advantage that because of the grid arrangement, well-defined intersections can be constructed. At these intersections, an organic semiconductor is placed between the two electrodes, in particular a quantum detector. By selectively activating the electrodes of the two layers, the entire area covered by the image detection component can be detected. By arranging the electrodes and quantum detectors in an appropriately fine structure, the resultant resolution capacity can be readily adjusted within very broad ranges.

The advantage of disposing the working electrode on the substrate is that the substrate can simultaneously serve as a mechanical carrier layer for the measuring device. To avoid affecting the measurement, the substrate is electrically non-conductive and the working electrode is separated from the substrate with an electrically isolating layer.

In another embodiment, the electromagnetic radiation of the electrochemiluminescence is predominantly emitted in the spectral range of 620 nm. However, the emission is not limited to this spectral range and in particular, emission in the entire visible and also near-infrared spectral range is possible, especially from 300 nm to 1500 nm, although the advantage of emission at 620 nm is that the radiation lies in the optical range of red visible light and existing image detection components usually exhibit a high spectral efficiency in this range. This is of particular advantage if it is necessary to detect reactions of very low intensity.

The invention will be explained in more detail below with reference to examples of embodiments illustrated in the appended drawings.

The drawings are schematically simplified diagrams illustrating the following:

FIG. 1 a) the device proposed by the invention with transparent or semitransparent working electrodes;

b) a cross-section, not drawn to scale;

FIG. 2 the device proposed by the invention with non-transparent working electrodes.

Firstly, it should be pointed out that the same parts described in the different embodiments are denoted by the same reference numbers and the same component names and the disclosures made throughout the description can be transposed in terms of meaning to same parts bearing the same reference numbers or same component names. Furthermore, the positions chosen for the purposes of the description, such as top, bottom, side, etc., relate to the drawing specifically being described and can be transposed in terms of meaning to a new position when another position is being described. Individual features or combinations of features from the different embodiments illustrated and described may be construed as independent inventive solutions or solutions proposed by the invention in their own right.

A transparent working electrode 2 is used with the embodiment of the device 1 for optoelectronically characterizing samples illustrated in FIG. 1. It is disposed on a substrate 3. The term working electrode in this context may also refer to more than one electrode.

The optoelectronic image detection component 4 is located between the substrate 3 carrying the working electrode 2 and another carrier layer 5, which serves as a support.

The optoelectronic image detection component 4 is made from a base of organic semiconductor.

FIG. 1 clearly shows that the overall construction is very compact because the image detection component is located directly underneath the working electrode.

During the process of electrochemiluminescence, a sample or reagent is placed on the working electrode 2, and an electric voltage is then applied across the working electrode 2 and the counter electrode 6, which brings about a reaction in the sample, leading to the emission of electromagnetic radiation 7, preferably in the optically visible spectral range. Since the image detection component 4 illustrated in FIG. 1 is disposed underneath the reaction area, the substrate 3 must be transparent or semitransparent in the relevant spectral range in order to ensure that the interaction of the electromagnetic radiation 7 with the image detection component 4 is as undistorted as possible. The substrate 3 may be made from glass for example, but transparent materials such as PET, COC, PS, PC, PP or PMMA are also possible.

The image detection component 4 preferably comprises a plurality of quantum detectors 8, which if necessary may be disposed on a carrier layer 5, in which case this carrier layer 5 may also serve as a stable basis for the device 1 proposed by the invention.

FIG. 1b illustrates a cross-section, not drawn to scale, of the device illustrated in FIG. 1a. The working electrode 2 is made from carbon, graphite, carbon nanotubes, for example, and also TCOs such as ITO for example, and disposed on the first flat face 9 of the substrate 3. To prevent electrical interference of the working electrode 2 and counter electrode 6, the substrate 3, particularly the first flat face 9, is electrically non-conductive.

As claimed, the image detection component 4 comprises a photoactive layer based on organic semiconductor 10, between two electrode layers. The first electrode layer 11, particularly the first electrode 12, is disposed on the second flat face 13 of the substrate 3. In order to ensure electrical isolation of the first electrode layer 11, the substrate 3 and the second flat face 13 are electrically non-conducting. An organic semiconductor 10 is disposed on the first electrode 12. The second electrode layer 14, in particular the second electrode 15, is disposed on the organic semiconductor 10. The first 11 and second 14 electrode layers, along with the organic semiconductor 10, constitute a part of the image detection component 4 and in particular form a quantum detector 8. For mechanical stability, another carrier layer 5 may be provided if necessary.

To ensure unhindered interaction of the electromagnetic radiation 7 generated by the electrochemiluminescence with the image detection component 4 or quantum detector 8, the substrate 3 and the first electrode layer 11 must be transparent or semitransparent. The electrodes 12 of the first electrode layer 11 may be made from transparent conductive oxides (TCOs), carbon nanotubes or thin metal layers, for example. The electrodes 12, 15 of the first 11 and second 14 electrode layers are preferably finger electrodes, disposed so that their lengths are oriented in different directions from each other, preferably by 90°. This arrangement results in a grid-like pattern of the quantum detectors, which enables a particularly high resolution to be obtained due to its compact construction FIG. 2 illustrates another embodiment of the device for optoelectronically characterizing samples by means of electrochemiluminescence as proposed by the invention, in which the working electrode is not transparent. To take a reading of the luminescence, the image detection component is positioned above the working electrode, and is so as closely as construction limitations allow.

The electrochemiluminescence occurs in chambers 16, for example, which surround the working electrode 2 and the counter electrode 6. An opening or a means of access is provided to enable the sample material to be introduced into the chamber. Since the working electrode 2 is not transparent in this embodiment, the image detection component 4 is located above the individual reaction chambers 16 and in particular is blocked from the reaction chambers by a carrier layer 17. The electromagnetic radiation 7 emitted due to electroluminescence is primarily emitted in the direction of the image detection means, in particular the quantum detectors 8 of the image detection component 4. The carrier layer 17 must therefore be transparent or semitransparent and is made from glass, for example, or from plastic such as PET, COC, PS, PC, PP or PMMA, for example.

Another important advantage of this embodiment is that the image detection component 4 and, optionally, the carrier layers 5 and 17 are such that they can also be retrospectively placed on the chambers filled with sample material.

The particular advantage of the two embodiments illustrated in FIGS. 1 and 2 is that integration of the image detection component offers an especially compact construction of the device for optoelectronically characterizing samples. In particular, the embodiment of the photoactive layer made from organic semiconductors has the further advantage, that the device proposed by the invention is especially inexpensive to manufacture, and is also well suited to one-off use due to the particularly advantageous properties relating to manufacture and the environment. The compact construction and inexpensive one-off use are also of particular advantage in mobile applications.

All figures relating to ranges of values given in the substantive description should be construed as meaning that they include any and all part-ranges, e.g. the range 1 to 10 should be understood as meaning that it includes all part-ranges starting from the lower limit of 1 and up to the upper limit of 10, i.e. all part-ranges start with a bottom limit of 1 or higher and end with an upper limit of 10 or less, e.g. 1 to 1.7 or 3.2 to 8.1 or 5.5 to 10.

The embodiments illustrated as examples represent possible design variants of the detection system, and it should be pointed out at this stage that the invention is not specifically limited to the design variants specifically illustrated, and instead the individual design variants may be used in different combinations with one another and these possible variations lie within the reach of the person skilled in this technical field given the disclosed technical teaching. Accordingly, all conceivable design variants that can be obtained by combining individual details of the design variants described and illustrated are possible and fall within the scope of the invention.

LIST OF REFERENCE NUMBERS

1 Device for optoelectronically characterizing samples
2 Working electrode
3 Substrate
4 Image detection component
5 Carrier layer
6 Counter electrode
7 Electromagnetic radiation
8 Quantum detector
9 First flat face
10 Organic semiconductor, photoactive layer
11 First electrode layer
12 First electrode
13 Second flat face
14 Second electrode layer
15 Second electrode
16 Reaction chamber
17 Carrier layer

The invention claimed is:

1. A device comprising an optoelectronic component for optoelectronically characterizing samples by means of electrochemiluminescence (ECL), said device comprising a counter electrode, a working electrode to which sample spots are applied and an optoelectronic component, in which, in order to excite the sample, an electric voltage is applied across the counter electrode and the working electrode, and wherein the optoelectronic component is embodied to read out the luminescence of the excited sample, wherein the optoelectronic component comprises an image detection component with a photoactive layer made from organic semiconductors between two electrode layers, and the working electrode is made from a transparent biocompatible material.

2. The device according to claim 1, wherein the optoelectronic image detection component is disposed flat underneath the working electrode.

3. The device according to claim 1, wherein the the optoelectronic image detection component is disposed flat directly above the working electrode.

4. The device according to claim 2, wherein the working electrode comprises carbon nanotubes (CNT).

5. The device according to claim 2, wherein the biocompatible material is selected from the group including TCOs, thin metal layers, along with very good electrically conducting organic materials such as polyaniline (PANI) und poly-3, 4-ethylene dioxythiophene (PEDOT).

6. The device according to claim 1, wherein the image detection component is printed onto a substrate.

7. The device according to claim 6, wherein the substrate is transparent or semitransparent.

8. The device according to claim 1, wherein the image detection component comprises a plurality of quantum detectors.

9. The device according to claim 1, wherein the electrode layers are finger electrodes arranged such that their lengths are oriented in different directions from each other.

10. The device according to claim 6, wherein the working electrode is disposed on the substrate.

11. The device according claim 1, wherein the electromagnetic radiation of the electrochemiluminescence is primarily emitted in the spectral range of about 620 ran.

* * * * *